United States Patent [19]

Fujii et al.

[11] Patent Number: 4,797,502

[45] Date of Patent: Jan. 10, 1989

[54] SULFONIC ACID ESTER DERIVATIVES AND PROCESS FOR PREPARING SAME

[75] Inventors: Setsuro Fujii, Toyonaka; Kazuo Ogawa, Tokushima; Toshihiro Hamakawa, Naruto; Yoshiyuki Muranaka, Tokushima, all of Japan

[73] Assignee: Taiho Pharmaceutical Company Limited, Tokyo, Japan

[21] Appl. No.: 4,610

[22] Filed: Jan. 20, 1987

Related U.S. Application Data

[60] Division of Ser. No. 861,635, May 7, 1986, Pat. No. 4,675,428, which is a continuation-in-part of Ser. No. 609,568, Apr. 30, 1984, abandoned.

[30] Foreign Application Priority Data

Sep. 6, 1982 [JP] Japan ................................. 57-155675
Nov. 24, 1982 [JP] Japan ................................. 57-206579

[51] Int. Cl.⁴ .......................................... C07C 143/68
[52] U.S. Cl. ....................................... 558/52
[58] Field of Search ............................. 558/52

[56] References Cited

U.S. PATENT DOCUMENTS 4,411,911  10/1983  Fujii et al. .................... 558/52
4,452,813   6/1984  Fujii et al. .................... 558/52

FOREIGN PATENT DOCUMENTS 2475041  8/1981  France .

Primary Examiner—Nicky Chan
Attorney, Agent, or Firm—Armstrong, Nikaido, Marmelstein & Kubovcik

[57] ABSTRACT

A sulfonic acid ester derivative represented by the general formula

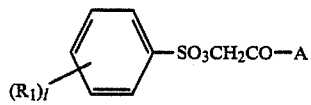

wherein $R_1$ is a hydrogen atom, alkyl having 1 to 4 carbon atoms or alkoxy having 1 to 4 carbon atoms, A is a group represented by the general formula

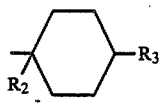

(wherein $R_2$ and $R_3$ are each alkyl having 1 to 4 carbon atoms) or by the general formula

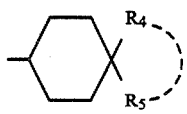

(wherein $R_4$ and $R_5$ are each alkyl having 1 to 4 carbon atoms or, when taken together with the carbon atom to which they are attached, form cycloalkyl having 4 to 6 carbon atoms), and l is an integer of from 1 to 3, and a process for preparing the derivative.

4 Claims, No Drawings

SULFONIC ACID ESTER DERIVATIVES AND PROCESS FOR PREPARING SAME

CROSS-REFERENCE TO RELATED APPLICATIONS

This application is a divisional application of Ser. No. 861,635, filed May 7, 1986, now U.S. Pat. No. 4,675,428, which was a continuation-in-part application of Ser. No. 609,568, filed Apr. 30, 1984, now abandoned, which was a national phase entry of PCT international application No. PCT/JP83/00300, filed Sept. 6, 1983.

TECHNICAL FIELD

This invention relates to novel sulfonic acid ester derivatives, and more particularly to antilipemic sulfonate derivatives and a process for preparing the same.

BACKGROUND ART

Hyperlipidemia is known to be a risk factor leading to various adult diseases, such as arteriosclerosis, cardio- and nephro-vascular diseases, diabetes, etc. The drugs for preventing or alleviating hyperlipidemia must have high safety because such drugs are likely to be used for a prolonged period of time in view of the nature of the disease. However, reports have been made on various side effects of nicotinic acid and derivatives thereof, dextran sulfate, and clofibrate and derivatives thereof heretofore known as antilipemic agents. Nicotinic acid and its derivatives, for example, produce side effects, such as pruritus and cutaneous flushing due to vasodilatation, gastrointestinal disorders, abnormalities in liver function and glucose intolerance. These drugs have many side effects further because they must be given at a large dose of at least 3 g/day. Furthermore clofibrate, which is typical of antilipemic agents which are widely used throughout the world, has recently been reported as having a carcinogenic activity as a serious side effect. Although animal tests or immunological investigations are being carried out on clofibrate by research institutes, the ultimate conclusions still remain to be made, so that clofibrate is clinically in limited use in various countries. In addition to the carcinogenic activity, clofibrate causes an increased sterol discharge, which reportedly increases the likelihood of gallstone formation. Thus the drug is likely to pose the problem of another side effect.

In view of the foregoing situation, we have conducted intensive research in order to provide more useful compounds having outstanding antilipemic activity and found that the compounds represented by the general formula (I) below fulfill this object. Thus the present invention has been accomplished.

DISCLOSURE OF THE INVENTION

The sulfonic acid ester derivatives of the present invention are represented by the following general formula.

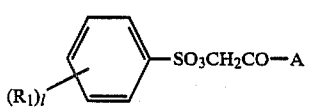
(I)

wherein $R_1$ is a hydrogen atom, alkyl having 1 to 4 carbon atoms or alkoxy having 1 to 4 carbon atoms, A is a group represented by the general formula

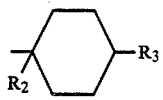

(wherein $R_2$ and $R_3$ are each alkyl having 1 to 4 carbon atoms) or by the general formula

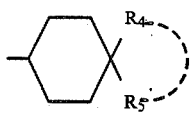

(wherein $R_4$ and $R_5$ are each alkyl having 1 to 4 carbon atoms or, when taken together with the carbon atom to which they are attached, form cycloalkyl having 4 to 6 carbon atoms), and l is an integer of from 1 to 3.

Examples of alkyl groups having 1 to 4 carbon atoms and represented by $R_1$, $R_2$, $R_3$, $R_4$ and $R_5$ of the general formula (I) are straight-chain or branched-chain alkyl groups such as methyl, ethyl, propyl, isopropyl, butyl, isobutyl and the like. Examples of alkoxy groups represented by $R_1$ and having 1 to 4 carbon atoms are straight-chain or branched-chain alkoxy groups such as methoxy, ethoxy, propyloxy, isopropyloxy, butoxy, isobutyloxy and the like. Examples of cycloalkyl groups which have 4 to 6 carbon atoms and which can be formed by $R_4$ and $R_5$ when they are taken together with the carbon atoms to which they are attached are cyclobutyl, cyclopentyl and cyclohexyl.

The compounds of the present invention represented by the general formula (I) include those having steric isomers. The invention includes all of these isomers.

Of the present compounds represented by the general formula (I), those wherein $R_1$ is a hydrogen atom are preferred. Other preferred compounds are those wherein A is a group represented by

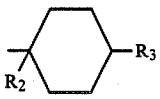

and the conformation of $R_2$ and $R_3$ is a cis form, and those wherein A is a group represented by

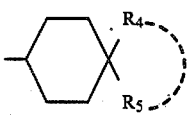

$R_4$ and $R_5$ being each alkyl having 1 to 3 carbon atoms or forming cyclopentyl or cyclohexyl when taken together with the carbon atom to which they are attached.

The compound of the invention represented by the general formula (I) can be prepared, for example, by a process wherein a diazo compound represented by the general formula

 (II)

wherein A has the same meaning as above is reacted with a sulfonic acid compound represented by the general formula

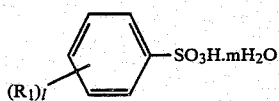

wherein $R_1$ and l have the same meanings as above, and m is 0, 1 or 2.

The above reaction is carried out usually in a solvent. While the solvent is not limited particularly insofar as it does not adversely affect the reaction, it is generally suitable to use dimethyl ether, diethyl ether, tetrahydrofuran, dioxane and like ethers; acetonitrile, chloroform, dichloromethane and like aprotic solvents; and petroleum ether, ligroin and the like. While the proportions of the diazo compound (II) and the sulfonic acid compound (III) to be used are suitably determined, it is generally advantageous to use at least one mole, preferably about 1.2 moles to about 2 moles, of the sulfonic acid compound (III) per mole of the diazo compound (II). The reaction temperature, although not limited particularly, is generally about $-10°$ to about $60°$ C., preferably about $0°$ C. to room temperature. The reaction proceeds favorably at this temperature.

The diazo compound (II) to be used as a material for the above reaction can be obtained usually by reacting thionyl chloride ($SOCl_2$) with a carboxylic acid (IV) to obtain a compound (V) and reacting diazomethane ($CH_2N_2$) with the compound as represented by the following reaction formula.

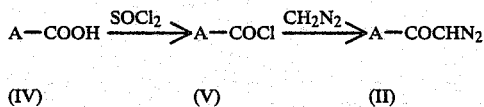

The reaction between the carboxylic acid compound (IV) and thionyl chloride, as well as the reaction between the resulting compound (V) and diazomethane, can be carried out by a usual method. For example, the reaction between the compound (V) and diazomethane is conducted advantageously under the temperature condition of about $-10°$ C. to room temperature in the same solvent as exemplified for the preparation of the compound of the present invention, using generally at least 2 moles of diazomethane per mole of the compound (V). The above reactions will be described in detail in the reference examples given later.

The compound (I) of the invention obtained by the foregoing process can be isolated by usual separating methods, for example, by column chromatography, recrystallization, vacuum distillation, etc.

The sulfonic acid ester derivatives (I) of the present invention thus obtained have esterase inhibiting activity, chymotripsin inhibitory activity, antilipemic activity, etc. and are useful as immunity controlling agents, antilipemic agents and the like. The present derivatives are especially superior in antilipemic effect to nicotinic acid and derivatives thereof, dextran sulfate, and clofibrate and derivatives thereof which are heretofore known as the effective components of antilipemic agents. Moreover the present compounds have the feature of being extremely low in toxicity, having a very wide range of safety and being higher in safety than the conventional antilipemic agents.

The compounds of the invention are formulated into various pharmaceutical preparations suited for routes of administration for use as drugs for man and animals making use of the foregoing pharmacological activities. Examples of such preparations are tablets, capsules, granules, powders and liquids for oral administration, and suppositories for non-oral administration.

Examples of useful excipients for preparing tablets, capsules, granules and powders are lactose, sucrose, starch, talc, magnesium stearate, crystalline cellulose, methyl cellulose, carboxymethyl cellulose, glycerin, sodium alginate and gum arabic. Also useful for such preparations are binders, such as polyvinyl alcohol, polyvinyl ether, ethyl cellulose, gum arabic, shellac and sucrose, glazing agents, such as magnesium stearate and talc, and usual coloring agents and disintegrators. Tablets can be coated by a known method. Useful liquid preparations are in the form of aqueous or oily suspensions, solutions, syrups, elixir, etc. These preparations are produced by usual methods.

Examples of useful base materials for preparing suppositories are oily or fatty materials such as cacao butter, polyethylene glycol, lanolin, fatty acid triglyceride, witepsol (fat, trademark of Dynamit Nobel A. G. of Germany), etc.

The dose of the drugs according to the invention can not be specifically defined but varies with the symptoms, body weight, age, etc. of the patient. Usually the present compound (active component) is given in an amount of about 50 to about 1500 mg/day for adults, preferably in two to four divided doses. The dose unit such as tablet or capsule preferably contains about 10 to about 1500 mg of the active component.

Given below are reference examples for the preparation of diazo compounds represented by the general formula (II) and useful for preparing compounds (I) of the invention, and examples wherein compounds (I) of the invention are prepared. Tables 1-(1), 1-(2), 2-(1) and 2-(2) show the compounds obtained in the examples and the properties thereof. The symbol "MS" listed stands for the result ($M^+$) of mass spectrum analysis, and "H-NMR" respresents the result of nuclear magnetic resonance spectrum analysis ($\delta$ value, ppm, in $CDCl_3$). The cis and trans conformations listed are based on the relation of $R_2$ and $R_3$.

REFERENCE EXAMPLE 1

To 5 g of 4,4-dimethyl-cyclohexylcarboxylic acid was added an excess of thionyl chloride, and the mixture was heated with stirring for 3 hours. After the reaction, the remaining thionyl chloride was distilled off in a vacuum, 10 ml of benzene was added to the residue and the mixture was distilled in a vacuum, giving oily 4,4-dimethylcyclohexylcarbonyl chloride.

Next at room temperature, 2.0 g of the 4,4-dimethyl-cyclohexylcarbonyl chloride obtained as above was added dropwise to 100 ml of an ether solution of diazomethane prepared from 10 g of nitrosourea, and the mixture was thereafter stirred at room temperature for about 1 hour. The solvent was distilled off from the reaction mixture in a vacuum, quantitatively giving pale yellow oily 1-diazo-2-(4,4-dimethyl-cyclohexyl)-2-ethanone (Compound I).

REFERENCE EXAMPLE 2

Compounds J, K and L listed in Table 1-(2) were prepared in the same manner as in Reference Example 1 except that 4,4-dimethyl-cyclohexylcarboxylic acid was replaced by 4-methyl-4-propyl-cyclohexylcarboxylic acid, spiro[4,5]-decane-8-carboxylic acid and spiro[5,5]-undecane-4-carboxylic acids were used respectively as materials.

REFERENCE EXAMPLE 3

An excess of thionyl chloride was added to 10 g of 4-isopropyl-1-methylcyclohexylcarboxylic acid (cis:trans=1:1, b.p.=122° C./2 mm Hg), and the mixture was stirred for 3 hours. The remaining thionyl chloride was distilled off in a vacuum from the resulting reaction mixture, and the oily product obtained was distilled in a vacuum to obtain 9.5 g of 4-isopropyl-1-methylcyclohexylcarbonyl chloride having a boiling point of 150° to 152° C./60 mm Hg. (Yield: 86.4%.)

Subsequently at room temperature, 5.0 g of the 4-isopropyl-1-methylcyclohexylcarbonyl chloride was added dropwise to 150 ml of an ether solution of diazomethane prepared from 15 g of nitrosourea, and the mixture was stirred at room temperature for about 2 hours. The solvent was distilled off from the reaction mixture in a vacuum, quantitatively giving pale yellow oily 1-diazo-2-(4-isopropyl-1-methylcyclohexyl)-2-ethanone (cis:trans=1:1).

The diazoketone compound in the form of a cis-trans mixture and obtained as above was separated off and purified by silica gel column chromatography (developing solvent: chloroform), giving 2.5 g of pale yellow oily 1-diazo-2-(trans-4-isopropyl-1-methylcyclohexyl)-2-ethanone (Compound C) from the first fraction and affording 2.4 g of pale yellow oily 1-diazo-2-(cis-4-isopropyl-1-methylcyclohexyl)-2-ethanone (Compound D) from the second fraction.

REFERENCE EXAMPLE 4

Compounds A, B, E, F, G and H listed in Table 1-(1) were prepared in the same manner as in Reference Example 3 from 1,4-diethyl-cyclohexylcarboxylic acid (cis:trans=3:1, b.p.=125°–128° C./4 mm Hg) or 4-isobutyl-1-methyl-cyclohexanecarboxylic acid (cis:trans=1:1, b.p=126°–128° C./2.5 mm Hg).

TABLE 1-(1)

$N_2CHCO$—[cyclohexane with $R_2$, $R_3$]

| Comp. | $R_2$ | $R_3$ | Conformation | Property | MS(M$^+$) | H—NMR |
|---|---|---|---|---|---|---|
| A | —$C_2H_5$ | —$C_2H_5$ | trans | oily | 208 | 5.44(s,1H), 2.22–1.96(d, 2H), 1.80–0.70(m, 17H) |
| B | —$C_2H_5$ | —$C_2H_5$ | cis | " | 208 | 5.40(s, 1H), 1.90–0.70(m, 19H) |
| C | —$CH_3$ | —CH(CH$_3$)$_2$ | trans | " | 208 | 5.45(s, 1H), 2.24–1.98(d, 2H, 1.74–0.75(m, 8H), 1.06(s, 3H), 0.82(d, 6H) |
| D | —$CH_3$ | —CH(CH$_3$)$_2$ | cis | " | 208 | 5.41(s, 1H), 1.80–0.75(m, 10H), 1.12(s, 3H), 0.87(d, 6H) |
| E | —$CH_3$ | —CH$_2$CH(CH$_3$)$_2$ | trans | " | 222 | 5.45(s, 1H), 2.24–1.90(d, 2H), 1.80–0.60(m, 10H), 1.06(s, 3H), 0.83(d, 6H) |
| F | —$CH_3$ | —CH$_2$CH(CH$_3$)$_2$ | cis | " | 222 | 5.42(s, 1H), 1.90–0.80(m, 12H), 1.12(s, 3H), 0.85(d, 6H) |
| G | —$CH_3$ | —$CH_2CH_3$ | trans | " | 194 | 5.45(s, 1H), 2.22–1.95(b, 2H), 1.75–0.70(m, 12H), 1.07(s, 3H) |
| H | —$CH_3$ | —$CH_2CH_3$ | cis | " | 194 | 5.41(s, 1H), 1.90–0.60(m, 14H), 1.12(s, 3H) |

TABLE 1-(2)

$N_2CHCO$—[cyclohexane with $R_4$, $R_5$ as spiro]

| Comp. | $R_4$ | $R_5$ | Property | MS(M$^+$) | H—NMR |
|---|---|---|---|---|---|
| I | —$CH_3$ | —$CH_3$ | oily | 180 | 5.26(s, 1H), 1.96–2.40(b, 1H), 1.00–1.80(m, 8H), 0.91(s, 6H) |
| J | —$CH_3$ | —$CH_2CH_2CH_3$ | oily | 208 | 5.27(s, 1H), 1.96–2.40(b, 1H), 1.00–1.80(m, 12H), 0.80–1.00(m, 6H) |

TABLE 1-(2)-continued $$N_2CHCO-\text{cyclohexyl}\begin{pmatrix}R_4\\R_5\end{pmatrix}$$

| Comp. | R₄ | R₅ | Property | MS(M⁺) | H—NMR |
|---|---|---|---|---|---|
| K | (CH₂)₄ (spiro ring) | | oily | 206 | 5.27(s, 1H), 1.96–2.40(b, 1H), 1.00–2.00(m, 16H) |
| L | (CH₂)₅ (spiro ring) | | oily | 220 | 5.27(s, 1H), 1.96–2.40(b, 1H), 0.80–1.96(m, 18H) |

EXAMPLE 1

A 0.2 g quantity of 1-diazo-2-(trans-1,4-diethylcyclohexyl)-2-ethanone (Compound A) was dissolved in 50 ml of ether, an excess of p-toluenesulfonic acid was added to the solution at room temperature, and the mixture was stirred until evolution of nitrogen gas ceased. The ethereal layer was washed with water and dried over anhydrous sodium sulfate. The solvent was distilled off from the dried layer in a vacuum, and the residue was subjected to silica gel column chromatography (developing solvent: chloroform) for separation and purification, giving 0.3 g of colorless crystalline 1-(p-methylbenzenesulfonyloxy)-2-(trans-1,4-diethylcyclohexyl)-2-ethanone (Compound 2) melting at 45° t 46° C. (Yield: 88.7%.)

EXAMPLE 2

Compounds 1 and 3–15 listed in Table 2-(1) were prepared from suitable starting materials in the same manner as in Example 1.

EXAMPLE 3

A 1.8 g quantity of 1-diazo-2-(4,4-dimethylcyclohexyl)-2-ethanone (Compound I) was dissolved in 50 ml of ether, 3.5 g of benzene sulfonic acid was added to the solution at room temperature, and the mixture was stirred until evolution of nitrogen ceased. The reaction mixture was washed with water and dried over anhydrous sodium sulfate. The solvent was distilled off from the dried mixture in a vacuum, and the resulting crystals were re-crystallized from ethanol, giving 2.5 g of 1-(benzenesulfonyloxy)-2-(4,4-dimethylcyclohexyl)-2-ethanone (Compound 16) melting at 34.5° to 35° C. (Yield: 80.6%.)

EXAMPLE 4

Compounds 17–26 listed in Table 2-(2) were prepared from suitable starting materials in the same manner as in Example 3.

TABLE 2-(1)

$$(R_1)_l-\text{phenyl}-SO_3CH_2CO-\text{cyclohexyl}(R_2)-R_3$$

| Comp. | R₁ | R₂ | R₃ | Conformation | M.p. or property | Yield (%) | MS(M⁺) | Elementary analysis or H—NMR (CDCl₃) |
|---|---|---|---|---|---|---|---|---|
| 1 | —H | —CH₂CH₃ | —CH₂CH₃ | tarns | oily | 76.9 | 338 | 8.01–7.85 (m, 2H) 7.76–7.40 (m, 3H) 4.88 (s, 2H) 2.35–1.96 (d, 2H) 1.80–0.50 (m, 14H), 0.69 (t, 3H) |
| 2 | 4-CH₃ | —CH₂CH₃ | —CH₂CH₃ | trans | 45–46 | 88.7 | 352 | C (%) H (%)<br>Calcd. 64.74 8.01<br>Found 64.85 8.03 |
| 3 | —H | —CH₂CH₃ | —CH₂CH₃ | cis | 48–49 | 73.8 | 338 | Calcd. 63.88 7.74<br>Found 63.47 7.62 |
| 4 | 4-CH₃ | —CH₂CH₃ | —CH₂CH₃ | cis | 57–58 | 82.7 | 352 | Calcd. 64.74 8.01<br>Found 64.94 8.05 |
| 5 | —H | —CH₃ | —CH(CH₃)₂ | trans | oily | 73.9 | 338 | 8.10–7.90 (m, 2H) 7.78–7.40 (m, 3H) 4.91 (s, 2H) 2.34–1.98 (d, 2H) 2.30–1.96 (d, 2H) 1.74–0.50 (m, 8H) |
| 6 | 2,4,6-CH₃ | —CH₃ | —CH(CH₃)₂ | trans | 74–75 | 54.8 | 380 | C (%) H (%)<br>Calcd. 66.28 8.48<br>Found 66.37 8.47 |

TABLE 2-(1)-continued (R₁)ₗ—C₆H₄—SO₃CH₂CO—C₆H₉(R₂)(R₃)

| Comp. | R₁ | R₂ | R₃ | Conformation | M.p. or property | Yield (%) | MS(M⁺) | Elementary analysis or H—NMR (CDCl₃) | | |
|---|---|---|---|---|---|---|---|---|---|---|
| 7 | —H | —CH₃ | —CH(CH₃)₂ | cis | 49–50 | 64.0 | 338 | Calcd. Found | 63.88 63.95 | 7.74 7.77 |
| 8 | 4-CH₃ | —CH₃ | —CH(CH₃)₂ | cis | 69–70 | 70.9 | 352 | Calcd. Found | 64.74 64.80 | 8.01 8.20 |
| 9 | —H | —CH₃ | —CH₂CH(CH₃)₂ | trans | 47–48 | 88.2 | 352 | Calcd. Found | 64.74 64.83 | 8.01 8.02 |
| 10 | 4-CH₃ | —CH₃ | —CH₂CH(CH₃)₂ | trans | 68–69 | 80.9 | 366 | Calcd. Found | 65.54 65.59 | 8.25 8.37 |
| 11 | —H | —CH₃ | —CH₂CH(CH₃)₂ | cis | 48–49 | 75.7 | 352 | Calcd. Found | 64.74 64.67 | 8.01 8.22 |
| 12 | 4-CH₃ | —CH₃ | —CH₂CH(CH₃)₂ | cis | 84–85 | 83.5 | 366 | Calcd. Found | 65.54 65.48 | 8.25 8.19 |
| 13 | 4-OCH₃ | —CH₃ | —CH₂CH(CH₃)₂ | cis | 62–63 | 77.5 | 382 | Calcd. Found | 62.80 62.57 | 7.91 7.83 |
| 14 | H | —CH₃ | —CH₂CH₃ | trans | oily | 66.5 | 324 | 8.04–7.85 (m, 2H) 7.75–7.40 (m, 3H) 4.91 (s, 2H), 2.25–1.90 (d, 2H) 1.76–0.50 (m, 12H) 1.04 (s, 3H) | | |
| 15 | H | —CH₃ | —CH₂CH₃ | cis | oily | 65.0 | 324 | 8.04–7.84 (m, 2H) 7.74–7.40 (m, 3H) 4.92 (s, 2H) 1.80–0.75 (m, 14H) 1.12 (s, 3H) | | |

TABLE 2-(2)

(R₁)ₗ—C₆H₄—SO₃CH₂CO—C₆H₉(R₄)(R₅)

| Comp. No. | R₁ | R₄ | R₅ | M.p. (°C.) or property | Yield (%) | MS(M⁺) | Elementary analysis or H—NMR (ppm) | C (%) | H (%) |
|---|---|---|---|---|---|---|---|---|---|
| 16 | H | —CH₃ | —CH₃ | 34.5–35 | 80.6 | 310 | Calcd. Found | 61.90 61.62 | 7.14 7.11 |
| 17 | 2,4,6-CH₃ | —CH₃ | —CH₃ | 70–71 | 54.7 | 352 | Calcd. Found | 64.74 64.69 | 8.00 7.67 |
| 18 | 4-OCH₃ | —CH₃ | —CH₃ | 105–106 | 60.5 | 340 | Calcd. Found | 59.97 59.65 | 7.10 7.20 |
| 19 | H | —CH₃ | —CH₂CH₂CH₃ | oily | 68.4 | 338 | 7.90–8.00 (m, 2H), 7.50–7.69 (m, 3H) 4.64, 4.52 (s, s, 2H), 2.20–2.60 (b, 1H) 1.00–1.80 (m, 12H), 0.80–1.00 (m, 6H) | | |

TABLE 2-(2)-continued $$(R_1)_l\text{-}C_6H_4\text{-}SO_3CH_2CO\text{-}C_6H_{10}(R_4)(R_5)$$

| Comp. No. | $R_1$ | $R_4$ | $R_5$ | M.p. (°C.) or property | Yield (%) | MS(M+) | Elementary analysis or H—NMR (ppm) | C (%) | H (%) |
|---|---|---|---|---|---|---|---|---|---|
| 20 | 4-CH₃ | —CH₃ | —CH₂CH₂CH₃ | 38–39.5 | 93.0 | 352 | Calcd. Found | 61.93 61.99 | 7.65 7.77 |
| 21 | 4-OCH₃ | —CH₃ | —CH₂CH₂CH₃ | 54–55 | 48.9 | 368 | Calcd. Found | 64.74 64.67 | 8.00 7.81 |
| 22 | H | —CH₂—CH₂—CH₂—CH₂— (spiro) | | 67–67.5 | 68.0 | 336 | Calcd. Found | 64.25 64.48 | 7.19 7.08 |
| 23 | 4-CH₃ | —CH₂—CH₂—CH₂—CH₂— (spiro) | | 80–81 | 85.3 | 350 | Calcd. Found | 65.11 65.35 | 7.47 7.65 |
| 24 | H | —CH₂CH₂CH₂CH₂CH₂— (spiro) | | 60.5–61 | 70.5 | 350 | Calcd. Found | 65.11 64.80 | 7.47 7.67 |
| 25 | 4-CH₃ | —CH₂CH₂CH₂CH₂CH₂— (spiro) | | 107–108 | 70.9 | 364 | Calcd. Found | 65.90 65.80 | 7.74 7.84 |
| 26 | 4-OCH₃ | —CH₂CH₂CH₂CH₂CH₂— (spiro) | | 118–119 | 58.7 | 380 | Calcd. Found | 63.13 63.20 | 7.41 7.35 |

Sulfonic acid ester derivatives of the present invention were subjected to the pharmacological tests to be described below.

1. Esterase inhibiting activity

A 10 micromole quantity of methyl butyrate in a 50% ethanol solution is added as a substrate to a specified amount of buffer solution containing 0.1 mole of trishydrochloric acid (pH 8.0). To the mixture is further added a 50% ethanol solution of the compound of the invention, immediately followed by addition of an esterase solution prepared from a purified microsome fraction of the liver of a rat (adjusted to hydrolyze 9 micromoles of methyl butyrate at 37° C. in one hour) as an enzyme solution. The mixture is reacted at 37° C. for 60 minutes.

After the reaction, alkaline hydroxylamine is added to the mixture to form a hydroxamic acid derivative of methyl butyrate, and a ferric salt is added to the derivative. The resulting red color is colorimetrically determined (at a wavelength of 540 nm) to determine the amount of remaining methyl butyrate. The esterase inhibiting ratios of the present compound at (at least three) different concentrations are plotted as ordinate, and the logarithms of the concentrations as abscissa to obtain a line, which gives the 50% inhibition concentration ($IC_{50}$).

2. Chymotripsin inhibiting activity

An enzyme solution (0.1 unit of chymotripsin) is added to a specified quantity of buffer solution containing 0.1 mole of trishydrochloric acid (pH 8.0). To the mixture is further added a 50% ethanol solution of the compound of the invention, and the resulting mixture is reacted at 37° C. for 20 minutes.

On completion of the reaction, 10 micromoles of N-acetyl-L-thyrosine (ATEE) serving as a substrate is added to the mixture, and the resulting mixture is reacted at 37° C. for 30 minutes. After the completion of the reaction, the amount of remaining ATEE is determined by the same hydroxamic acid method as used in the method of determining the esterase inhibiting activity. The percent chymotripsin inhibition is given by $$\text{Percent inhibition} = (A - B)/A \times 100$$

wherein A is the amount of hydrolyzed esters in the reaction system not containing the compound of the invention, and B is the amount of hydrolyzed esters in the reaction system containing the present compound.

3. Antilipemic effect

Seven-week-old male Wistar rats weighing 200 to 220 g are used, 5 rats in each group.

The compound of the invention (100 mg) is dissolved in 5 ml of olive oil. The olive oil containing the compound is orally given to the rat with a probe at a dose of 5 ml/kg. Two hours thereafter, 6 ml of whole blood is withdrawn from the descending aorta of the rat under ether anesthesia with a syringe containing heparin. The blood is centrifuged at 5° C. and 3000 r.p.m. to obtain the plasma.

The plasma collected is used for determining the triglycerides content, using a triglycerides measuring kit (trademark "Triglycerides-B Test Wako," product of Wako Junyaku Co., Ltd., Japan). Olive oil containing no compound is similarly given to a control group, while no treatment is conducted for a normal group. The triglycerides content in the plasma is also determined for these groups in the same manner as is the case with the test groups.

The percent hyperlipidemia inhibition achieved by the present compound is given by Percent inhibition = $(A-C)/(A-B) \times 100$ in which A is the triglycerides content of the control group, B is the triglycerides content of the normal group, and C is the triglycerides content of the group to which the present compound is given.

Table 3 shows the results of the pharmacological tests 1 to 3 achieved by compounds of the invention. In Table 3, triglycerides inhibition is expressed as "TG inhibition.".

TABLE 3

| Comp. No. | Antilipemic TG inhibition (%) | IC$_{50}$ for esterase ($\times 10^{-6}$ mole) | Chymotripsin inhibition (%) ($1 \times 10^{-4}$ mole) |
|---|---|---|---|
| 1 | — | 35 | 12 |
| 3 | 47.1 | 0.34 | 25 |
| 5 | 49.0 | 33 | 14 |
| 7 | 72.0 | 0.016 | 26 |
| 8 | — | 0.56 | 35 |
| 11 | 70.5 | 2.2 | 15 |
| 16 | 77.5 | 0.0058 | 71 |
| 17 | — | 0.0020 | — |
| 18 | — | 2.5 | — |
| 19 | 95.4 | 0.0042 | 34 |
| 22 | 84.2 | 0.022 | 41 |
| 23 | — | 3.0 | — |
| 24 | 93.5 | 0.0054 | 61 |

We claim:

1. A sulfonic acid ester derivative represented by the general formula

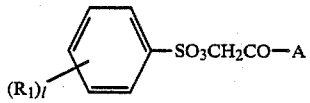

wherein $R_1$ is a hydrogen atom, alkyl having 1 to 4 carbon atoms or alkoxy having 1 to 4 carbon atoms, A is a group represented by the general formula

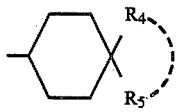

wherein $R_4$ and $R_5$ are each alkyl having 1 to 4 carbon atoms or, when taken together with the carbon atom to which they are attached, form cycloalkyl having 4 to 6 carbon atoms, and l is an integer of from 1 to 3.

2. A derivative as defined in claim 1 wherein $R_1$ is a hydrogen atom.

3. A derivative as defined in claim 1 wherein $R_4$ and $R_5$ are each alkyl having 1 to 3 carbon atoms.

4. A derivative as defined in claim 1 wherein $R_4$ and $R_5$ form cycloalkyl having 5 or 6 carbon atoms when taken together with the carbon atom to which they are attached.

* * * * *